(12) United States Patent
Nauschnegg

(10) Patent No.: US 10,086,368 B2
(45) Date of Patent: Oct. 2, 2018

(54) MOVABLE MEASUREMENT CELL

(71) Applicant: EXIAS Medical GmbH, Graz (AT)

(72) Inventor: Gerald Nauschnegg, Graz (AT)

(73) Assignee: EXIAS Medical GmbH, Graz (AT)

( * ) Notice: Subject to any disclaimer, the term of this patent is extended or adjusted under 35 U.S.C. 154(b) by 205 days.

(21) Appl. No.: 15/257,701

(22) Filed: Sep. 6, 2016

(65) Prior Publication Data

US 2017/0065970 A1    Mar. 9, 2017

(30) Foreign Application Priority Data

Sep. 7, 2015 (DE) .................... 10 2015 114 951

(51) Int. Cl.
*G01N 35/10* (2006.01)
*G01N 33/49* (2006.01)
(Continued)

(52) U.S. Cl.
CPC .............. *B01L 3/502* (2013.01); *G01N 33/49* (2013.01); *G01N 33/492* (2013.01); *G01N 35/1011* (2013.01); *G01N 35/1079* (2013.01); *B01L 2200/12* (2013.01); *B01L 2200/147* (2013.01); *B01L 2300/0627* (2013.01);
(Continued)

(58) Field of Classification Search
CPC .......... B01L 2200/12; B01L 2200/147; B01L 2300/0627; B01L 2300/0672; B01L 2300/0838; B01L 2300/0887; B01L 2300/123; B01L 2300/18; B01L 3/502; G01N 2035/00356; G01N 33/49; G01N 33/492; G01N 35/1011; G01N 35/1079
See application file for complete search history.

(56) References Cited

U.S. PATENT DOCUMENTS 4,570,495 A    2/1986  Terada
5,338,435 A *  8/1994  Betts .................. A61B 5/15003
                                                    204/406
(Continued)

FOREIGN PATENT DOCUMENTS

DE        692 16 485 T2    7/1997
DE   11 2005 001 985 T5    7/2007
(Continued)

OTHER PUBLICATIONS

Communication with Extended European Search Report issued for Application No. 16187681; search completed Dec. 20, 2017; dated Jan. 3, 2017; 7 pages.
(Continued)

*Primary Examiner* — Jennifer Wecker
(74) *Attorney, Agent, or Firm* — Lewis Roca Rothgerber Christie LLP

(57) ABSTRACT

A movable measurement cell for measuring at least one constituent of a liquid sample, in particular blood, having a first portion comprising a measurement system having at least one sensitive area at a surface of the first portion: a second portion having at least a part of a reception space for the sample, the second portion is connected to the first portion such that the sample is in contact with the sensitive area when the sample is located within the reception space, and a sample supply system attached to an inlet to allow supply of a liquid sample into the reception space.

17 Claims, 5 Drawing Sheets

(51) Int. Cl.
  *B01L 3/00* (2006.01)
  *G01N 35/00* (2006.01)
(52) U.S. Cl.
  CPC ............... *B01L 2300/0672* (2013.01); *B01L 2300/0838* (2013.01); *B01L 2300/0887* (2013.01); *B01L 2300/123* (2013.01); *B01L 2300/18* (2013.01); *G01N 2035/00356* (2013.01)

(56) References Cited

U.S. PATENT DOCUMENTS

| | | | |
|---|---|---|---|
| 5,342,498 | A | 8/1994 | Graves et al. |
| 5,646,046 | A | 7/1997 | Fischer et al. |
| 5,718,816 | A | 2/1998 | Savage et al. |
| 5,795,552 | A | 8/1998 | Corby et al. |
| 6,343,223 | B1 | 1/2002 | Chin et al. |
| 7,186,384 | B2 | 3/2007 | Rüther et al. |
| 8,158,430 | B1 | 4/2012 | Roy et al. |
| 8,206,650 | B2 | 6/2012 | Samsoondar |
| 8,357,336 | B2 | 1/2013 | Gulo |
| 8,491,185 | B2 * | 7/2013 | Steinboeck ........ G01N 33/4925 374/10 |
| 9,415,390 | B2 | 8/2016 | Gumbrecht et al. |
| 2005/0130292 | A1 | 6/2005 | Ahn et al. |
| 2006/0078873 | A1 | 4/2006 | Ogawa et al. |
| 2006/0140822 | A1 * | 6/2006 | Krysl ................... G01N 27/403 422/108 |
| 2008/0138890 | A1 | 6/2008 | Horiike et al. |

FOREIGN PATENT DOCUMENTS

| | | |
|---|---|---|
| DE | 10 2009 043 226 B4 | 3/2011 |
| EP | 1 347 282 A2 | 9/2003 |
| EP | 1 674 866 A1 | 6/2006 |
| EP | 1 852 704 A2 | 11/2007 |
| EP | 2 037 280 A1 | 3/2009 |
| EP | 2 199 792 A1 | 6/2010 |
| WO | WO 95/06867 A1 | 3/1995 |
| WO | WO 2005/010497 A2 | 2/2005 |

OTHER PUBLICATIONS

DPMA Search Report dated Oct. 8, 2015, for corresponding German Patent Application No. 10-2015-114951.6 (7 pages).

* cited by examiner

MOVABLE MEASUREMENT CELL

CROSS-REFERENCE TO RELATED APPLICATION

The subject application claims priority to the benefit of German Patent Application number 10 2015 114 951.6, filed on Sep. 7, 2015, the entire content of which is incorporated herein by reference.

FIELD OF INVENTION

The present invention relates to a movable measurement cell for measuring at least one constituent of a liquid sample, in particular blood. The present invention further relates to a measurement apparatus for measuring at least one constituent of a liquid sample, the measurement apparatus comprising the movable measurement cell. Further, the present invention relates to a method for manufacturing a movable measurement cell and still further relates to a method for measuring at least one constituent of a liquid sample.

ART BACKGROUND

For measuring parameters of a blood sample, such as blood gases, electrolytes and metabolites, an accurate control of the temperature of the sample to be examined may be required. Samples may be supplied into a conventional measurement apparatus at different temperatures, such as for example between 4° C. and 41° C. The measurement of the blood parameters is however required to be performed at a fixed temperature, such as 37° C. Such a temperature may for example be required to measure a partial pressure of oxygen, a partial pressure of carbon dioxide, to measure a pH or to measure an electrolyte concentration, such as calcium, sodium, potassium or chloride ions.

It may take some time to adjust the temperature of the sample to the intended measurement temperature. Furthermore, a measurement time is influenced by the time required to supply the sample into the measurement cell in the measurement apparatus. Further, the measurement time may be dependent on maximally possible pump velocities.

Furthermore, a measurement accuracy may depend on a possible change of the sample on the way from the external sample source to the measurement sensors due to carry-over effects (i.e. dilution). Also a possible entrapment of air bubbles may result in wrong measurements. The carry-over effects as well as the entrapment of air bubbles may most likely happen on positions where the material of the sample path changes. Different materials (e.g. steel, plastic, rubber, material of the sensor (casing) etc.) with which the sample may be in contact during supply to the measurement apparatus or during measurement itself may therefore influence the result of the measurement and thus may influence the measurement accuracy.

The required accuracy of the temperature regulation or temperature control may for example be 37° C.+/−0.2° C. Such accuracy of the temperature regulation may be required due to the temperature dependency of the solubility of gases within blood and within aqueous solutions, as well as the temperature dependency of the pH value for example. It may further be desired to use as little amount of sample as possible, while maintaining measurement accuracy. In this respect, the wetting properties of different materials of the measurement cell as well as the sample supply path may be relevant and also the constructional design of the measurement cell.

In conventional measurement systems, the sample may be heated along a pre-heating path which is integrated within the measurement apparatus. Other arrangements or concepts of the prior art directly heat up the sample within the measurement chamber by positioning the measurement cell or measurement chamber between voluminous heating blocks. Other systems of the prior art use measurement cells with sensor substrates having printed thereon resistance traces and a printed temperature sensor for changing and controlling the temperature of the sample, the measurement cell directly attached to the measurement apparatus in a fixed position.

The European patent application EP 1 674 866 A1 discloses an arrangement for controlling the temperature of a measurement cell, wherein the measurement cell comprises a measurement channel in which a sensor element is arranged and an analyzer having a surface that can be temperature-controlled. The measurement cell can exchangeably be inserted into the analyzer and may be brought in contact with the surface which may be temperature-controllable. A heat conducting elastic or plastic layer is attached on a measurement cell wall or the surface which may be temperature-controllable.

The European patent application EP 2 199 792 A1 discloses a method for examining the quality of a thermal coupling of a measurement cell, wherein the measurement cell is exchangeably insertable into an analyzer and comprises at least one sensor element within a measurement channel. The measurement channel is filled with a calibration liquid and a rapid temperature change is applied on the element which may be temperature-controllable and with which the measurement cell is in mechanical contact. Further, a time course of a signal of the at least one sensor element is acquired and the quality of the thermal coupling is determined based on an analysis of the time course of the signal.

U.S. Pat. No. 5,342,498 discloses an improved electronic wiring board having a thermistor and at least one blood gas sensor supported, in close relation, one to the other, on one side of the board and a heater supported on the other side of the board to provide heat in response to temperature sensed by the thermistor, to at least the region where the thermistor and the blood gas sensor are positioned on the board to control the temperature of the region of the board within a narrow distribution of temperatures.

U.S. Pat. No. 5,718,816 describes a sensor cartridge into which sensors are installed, wherein a plurality of inner walls within the housing locate a pump tube assembly and right angle fluid coupling within the housing. An opening in the housing receives a first boss which extends from the blood analyzer. A capture/release arm has an opening through which the first boss protrudes. The arm is resiliently held in place such that an inner edge of the opening is captured within a ring-like groove in the boss that extends from the blood analyzer when the cartridge is installed in the blood analyzer. Electrical contacts of the connector on the rear side of the sensor assembly are aligned to mating electrical contacts of the blood analyzer as the sensor assembly is being installed by alignment of the boss which extends from the blood analyzer to mate with the boss which extends from the housing, and alignment of two male fluid connectors.

Most measurement systems and methods of the prior art have the disadvantage that a voluminous, heavy heating block and/or a pre-tempering path and/or a heated measurement chamber are used, to satisfy the requirements of the temperature control during the measurement. The heating block or the pre-tempering path are, due to cost issues, to be arranged within the measurement apparatus and cannot be placed into a consumable. Further, the thermal coupling between the heating block and the actual measurement cell is unknown and needs to be examined, as discussed in the above cited application EP 2 199 792 A1. The quality of the thermal coupling strongly influences the velocity or speed of arriving at a temperature of the sample that is required for the measurement.

Another measurement system and method of the prior art has the disadvantage that a measurement cell with a heated sensor substrate is to be placed in a fixed position at the analysator. This arrangement requires to extended tubing paths, resulting in a higher demand of calibration liquids and a higher time effort for supplying these liquids. Another disadvantage of this setup is that the sample input system has to be rotatably coupled to the measurement cell requiring a sealing element between the sample supply system and the measurement cell.

In prior art solutions, the position of the measurement cell is fixed within the measurement apparatus. The supply of the sample thus necessarily is performed using extending tubing resulting in a change/modification of the sample within the supply tubing. Further, the required minimal sample volume is negatively affected. Due to the extensive tubing paths, also the minimally achievable measurement times are limited by a lower limit (for example 35 s) thereby lowering throughput.

There may be a need for a movable measurement cell for measuring at least one constituent of a liquid sample, for a measurement system for measuring at least one constituent of a liquid sample, for a method for manufacturing a movable measurement cell and for a method for measuring at least one constituent of a liquid sample, wherein at least one of the above-mentioned disadvantages of the prior art are attenuated, reduced or even avoided.

In particular, it may be desired to achieve a measurement cell that allows an accurate measurement of at least one constituent of a liquid sample in a reliable manner, in a sufficiently short measurement time and requiring a sufficiently low amount of sample. Furthermore, it may be desired to provide a measurement cell which may easily be manufactured and which allows convenient feeding of a sample from different source containers in particular having a short sample supply path.

SUMMARY OF THE INVENTION

The need is satisfied by the subject-matter of the independent claims which are directed to a movable measurement cell for measuring at least one constituent of a liquid sample, which are directed to a measurement apparatus for measuring at least one constituent of a liquid sample, which are directed to a method for manufacturing a movable measurement cell and which are further directed to a method for measuring at least one constituent of a liquid sample.

According to an embodiment of the present invention it is provided a movable measurement cell for measuring at least one constituent of a liquid sample, in particular whole blood, the measurement cell including a first portion comprising a measurement system having at least one sensitive area at a surface of the first portion, a second portion comprising a at least a part of a reception space for the sample, the second portion being connected to the first portion such that the sample is in contact with the at least one sensitive area when the sample is located within the reception space, and a sample supply system attached to an inlet (e.g. located or fixed at the first portion and/or at the second portion) to allow supply of a liquid sample into the reception space. The sample supply system may be fixedly attached to the inlet, not allowing deformation or movement. The sample supply system may be made from solid and/or non-bendable material(s) and may be stiff.

The sample supply system may be adapted to supply a fluid sample to the reception space from a sample container providing access to a surface of the liquid sample, in particular without requiring any (bendable or flexible) tubing or any elastomeric sealing. The supply system may not change shape and/or may not deform during supply of the sample into the reception space.

The movable measurement cell may in particular be moved for feeding a sample from an external source via the sample supply system and the inlet of the measurement cell into the reception space. Different sample source containers or external equipment providing the sample may require different orientations or configurations of the sample supply system in order to be able to feed the sample from the external source into the reception space. The sample supply system may be fixedly attached to the inlet (in one embodiment being arranged at the second portion of the measurement cell, in another embodiment being arranged at the first portion of the measurement cell). Thus, during feeding a sample from different sample sources, the sample supply system remains attached to the inlet in a position and orientation fixed relative to the rest of the measurement cell. However, the whole measurement cell may be moved (for example translated and/or rotated or turned) in order to arrange the sample supply system (in particular regarding orientation) such that the sample can be filled from the external source or external container into the sample supply system which in turn supplies the sample via the inlet into the reception space for measurement.

The measurement system may in particular be adapted to measure the concentration of at least one ion, such as $K^+$, $Ca^{++}$, $Na^+$, $Cl^-$, and/or pH and/or partial pressures of $O_2$, $CO_2$ and/or concentrations of Glucose, Lactate, Urea, Creatinine or the like. For each particular analyte, at least one separate respective sensitive area may be provided. When several sensitive areas for measurement of different constituents of the liquid are provided, the sensitive area may be arranged side by side along a longitudinal direction of the reception space.

The measurement system may be adapted to perform potentiometric and/or amperometric measurement and/or conductometric measurements i.e. measurements of electrical potentials and/or electric currents and/or electric impedances. As measurement result, concentration of different analytes may be determined and/or the values of the partial pressures of different gases within the sample may be determined and/or the volumetric amount of blood cells and output. The measurement system may alternatively or additionally also be adapted to perform optical measurements.

The reception space may in particular be configured as a channel having a longitudinal direction corresponding to a flow direction during supply of the sample into the reception space. The reception space comprised in the second portion may be formed as a channel or as a groove and the reception space may be (at least partly) closed when the first portion is connected to the second portion. The reception space may be accessed after connecting the second portion to the first portion via the inlet and/or via an outlet (in particular e.g. at the second portion).

The second portion may be integrally formed and may not comprise any electrically conducting material. The second portion may in particular serve as a casing providing an enclosure to define the reception space or measurement channel. The reception space will also be referred to as measurement channel. The first portion may be glued to the second portion or may be connected by other means. A seal may be arranged between interfaces of the first portion and the second portion in order to tightly seal the reception space.

The sample supply system allows supplying a sample from different source containers into the reception space via for example a supply tube, such as a supply needle made from an inert metal or any (in particular biocompatible) material matching the requirements for this application, e.g. some polymeric material. Thereby, deterioration of the sample may be reduced and the supply length may be limited to the length of the sample supply system.

According to an embodiment of the present invention, the sample supply system includes a supply needle connected at one end to the inlet having a lumen in communication with the reception space.

The supply needle may be straight and may have a length between 3 cm and 20 cm. Thereby, a short supply length may be provided. For feeding a sample from an external container into the reception space, another end of the supply needle may be immersed into the sample contained in an open external container, while the other end of the supply needle is vertically arranged at a lower level than the one end of the needle that is connected to the inlet. For feeding a sample from other external sources, the supply needle may be oriented differently, for example such that the one end is vertically at a lower level than the other end of the supply needle. Thereby, samples from different sample sources may conveniently be fed into the reception space for measurement by previously appropriately orienting/positioning (i.e. moving in general) the movable measurement cell.

According to an embodiment of the present invention, the sample supply system further includes an elastomer element having a through hole, the supply needle being at least partially inserted into the through hole. The supply needle is in a fixed orientation coupled to the first and/or second portion.

The elastomer may comprise rubber and the elastomer element may in particular have (optionally in some embodiments) a rotational symmetry, the symmetry axis in particular running along a longitudinal axis of the through hole. In other embodiments the elastomer element does not have any symmetry. The elastomer element may, when engaged into a supporting portion, support and protect the supply needle. Furthermore, the elastomer element may allow connection of a capillary, while the supply needle is at the other end partly inserted into the through hole such that the other end of the needle and an end of the capillary contact each other (or are at least close apart from each other) at a center of the through hole, thereby allowing feeding a sample originally located within the capillary into the supply needle for supply of the sample into the reception space.

According to an embodiment of the present invention, the supply needle is adapted to allow supply of a sample from a syringe or from a vacutainer, wherein the supply needle being partially inserted into the through hole of the elastomer element from one side allows supply of a sample from a capillary while the capillary is partially inserted into the through hole of the supply needle from another side.

Thereby, a number of conventionally used sample containers or sample source equipment is supported.

According to an embodiment of the present invention, the movable measurement cell further comprises a heating/temperature detection system integrated into the first portion.

The heating/temperature detection system may be adapted for both heating and temperature detection. The heating/temperature detection system may in particular be adapted to heat the sample when located within the reception space. The heating/temperature detection system may be electrically insulated from the sample when arranged or located or present within the reception space. The heating/temperature detection system may be located close to the reception space, such as 0.02 mm to 1.5 mm away from the reception space, in particular from the sensitive area of the measurement system.

The heating/temperature detection system may further include a control system that is adapted to operate a heating system and a temperature detection system of the heating/temperature detection system, in order to change and maintain the temperature of the sample supplied to the reception space. Thereby, the measurement of the at least one constituent may be performed at a defined temperature.

Thereby, a simple heating/temperature detection system is provided requiring a simple construction. Heating may be performed by running an electric current through the heating wire. Temperature detection may be performed by measuring a resistance of the heating wire, wherein the resistance may depend on the temperature. The heating wire may be arranged in the meandering manner such that the heating wire multiple times crosses (when viewed in projection) the measurement channel, without electrically contacting a sample within the reception space. Thereby, a homogeneous temperature profile, in particular constant temperature, along the longitudinal direction of the measurement channel may be achieved. Thereby, the measurement accuracy may be improved.

According to an embodiment of the present invention, the first portion comprises a polymer formed as a printed circuit board. The polymer may effectively adhere to the second portion when a conventionally available adhesive is used. Further, manufacturing the first portion may thereby be simplified. In particular, a conventionally available printed circuit board material may be used and conventionally available techniques may be applied to form copper conductive traces and/or sensor areas and/or other electronic elements onto the polymer according to the requirements of the measurement system and the requirements of the heating/temperature detection system. The printed circuit board may be layered.

According to an embodiment of the present invention, the printed circuit board comprises several layers including a first layer including the measurement system, and (at least) a second layer having an upper surface attached to a lower surface of the first layer and including a heating/temperature detection system, wherein an upper surface of the first layer is attached, in particular using an adhesive, to the second portion to partly close the reception space.

Thereby, manufacturing of the first portion may be simplified, while enabling an accurate measurement, while the temperature of the sample is controlled.

According to an embodiment of the present invention, the several layers further include and are attached to each other in that order: a third layer including a heat conducting material for distributing heat generated by the heating/temperature detection system; and/or a fourth layer including an electrically conducting material for electrical shielding; and/or a fifth layer including a heating/temperature detection system; and/or a sixth layer including an electrically conducting material for electrical shielding. Other orders of layers and other numbers of layers may be possible. The number of layers and order of layers may be selected depending on the application.

The additional layers may be optional but may improve homogeneity of the temperature distribution and/or may reduce the influence of disturbing electrical or electromagnetic signals.

According to an embodiment of the present invention, the material of the printed circuit board comprises a fibre-reinforced polymer, fibres of the fibre-reinforced polymer in particular including at least one of glass, carbon, aramid, basalt, paper, wood, asbestos, wherein the polymer in particular comprises a at least one of epoxy, vinylester, polyester thermosetting plastic, phenol formaldehyde. Thereby, conventionally available polymer material may be used, simplifying the manufacturing of the measurement cell and reducing the costs of the measurement cell.

According to an embodiment of the present invention, the second portion is integrally formed, in particular manufactured by injection molding, further in particular using polycarbonate and/or blends of polymers. Thereby, manufacturing of the first portion may be simplified and costs may be reduced. Further, connecting the first portion with the second portion may be achieved by gluing the first portion to the second portion using a conventionally available adhesive.

It should be understood that features individually or in any combination described, mentioned or provided for a movable measurement cell are also, individually or in any combination applicable or employable to a measurement apparatus for measuring at least one constituent of a sample, to a method for manufacturing a movable measurement cell and to a method for measuring at least one constituent of a sample according to an embodiment of the present invention and vice versa.

According to an embodiment of the present invention, it is provided a measurement apparatus for measuring at least one constituent of a liquid sample, the measurement apparatus comprising: a movable measurement cell according to one of the preceding embodiments further comprising a trail engagement portion; a mounting system for movably mounting the movable measurement cell, the mounting system including: a bar having a guiding trail; and a supporting portion at one end of the bar for supporting the supply needle, wherein the trail engagement portion of the measurement cell is engageable with the guiding trail for moving the movable measurement cell in a direction of the guiding trail being along a longitudinal direction of the supply needle.

The measurement apparatus may further comprise a data processing module for processing measurement data obtained from the measurement system, an energy supply system for providing electrical energy to components (such as the measurement system, heating/temperature detection system(s)) of the measurement cell, pump(s), valve(s), a user interface, external network capability, access to a database, etc.

The bar may also be formed as a frame allowing to move the movable measurement cell along a straight translation path and also allowing the swivel or rotate of pivot the measurement cell. The moving distance may amount to between 3 cm and 15 cm, the cell may be rotated by 10 to 90 degrees or even further. The bar may have a length between 3 cm and 15 cm. The measurement cell engaged with the guiding trail may be shifted (for example by hand) along the guiding trail. The measurement cell may for example comprise as trail engagement portion one (or more) protrusions (in particular integrally formed with the second portion) being inserted into and/or protruding through a slit representing the guiding trail. Other configurations are possible. When the measurement cell is shifted towards another end of the bar, the trail engagement portion may be disengaged from the guiding trail for removing the measurement cell from the mounting system. For example, when the guiding trail is provided as a slot, the slot may have at the other end of the bar, an enlarged opening through which ends of the trail engagement portion of the measurement cell may be withdrawn for removal of the measurement cell (e.g. for maintenance or replacement). Also the bar may be manufactured from a polymer, in particular manufactured using injection moulding.

According to an embodiment of the present invention, the supporting portion of the mounting system is adapted to circumferentially engage the elastomer element, thereby clamping the elastomer element while the supply needle is at least partially inserted into the through hole of the elastomer element. The supporting portion may prohibit bending of the supply needle.

According to an embodiment of the present invention, the measurement apparatus further comprises a base, wherein the measurement cell is rotatably fixed at one point to the base, thereby allowing to pivot the measurement cell around the one point to orient the supply needle such that the end connected to the inlet of the measurement cell is selectively vertically at a higher position, at a same position or at a lower position than another end of the supply needle into which the sample is supplied from an external source, wherein the bar is in particular, at another end apart from the one end where the supporting portion is arranged, rotatably fixed at a portions of the base that can rotate around a rotation center. Thereby, feeding samples from different source equipment into the reception space of the movable measurement cell is enabled.

The measurement apparatus may further comprise a washing plate, being fixed at the base and having a through hole, wherein when the movable measurement cell is appropriately pivoted, the elastomer element contacts the washing plate and seals fluid supplied to the through hole of the washing hole such that the fluid is guided through the through hole of the elastomer element and the lumen of the supply needle to enter the reception space. The washing plate may serve as a fluidic coupling means between the inlet of the measurement cell and washing and/or calibration solutions and/or reagents. Washing and/or calibration solutions may be introduced into the measurement cell via the washing plate.

According to an embodiment of the present invention it is provided a method for manufacturing a movable measurement cell for measuring at least one constituent of a liquid sample, the method comprising: manufacturing a first portion comprising a measurement system having at least one sensitive area at a surface of the first portion; manufacturing, in particular by injection moulding, a second portion comprising a at least a part of a reception space for the sample; connecting the second portion and the first portion such that the sample is in contact with the at least one sensitive area when the sample is located within the reception space; and attaching a sample supply system to an inlet (e.g. at the second portion) to allow supply of a liquid sample into the reception space.

The first portion may be manufactured by layering several layers each layer comprising circuitry or shielding or heat generation or temperature distribution or temperature measurement equipment. Thereby, conventional methodology may be utilized.

According to an embodiment of the present invention it is provided a method for measuring at least one constituent of a liquid sample, the method comprising: providing a movable measurement cell for measuring at least one constituent of a liquid sample, the measurement cell including: a first portion comprising a measurement system having at least one sensitive area at a surface of the first portion; a second portion comprising a at least a part of a reception space for the sample, the second portion being connected to the first portion such that the sample is in contact with the at least one sensitive area when the sample is located within the reception space; and a sample supply system attached to an inlet (e.g. at the second portion) to allow supply of a liquid sample into the reception space; moving the movable measurement cell such that the sample supply system is in a configuration, in particular a position and/or an orientation, to allow feeding a liquid sample from an external source into the sample supply system.

The method for measuring may further comprise operating the heating/temperature detection system in order to achieve a desired measurement temperature of the sample located within the reception space and to maintain this desired temperature. The desired temperature may for example be 37° C. The accuracy of the temperature control may for example achieve a temperature of 37° C.+/−0.2° C.

According to an embodiment of the present invention, the temperature control (including heating and/or measurement and/or regulation of the temperature to achieve a constant temperature) may be directly integrated into the measurement cell, in particular in the polymeric sensor substrate (printed circuit board material). The sample supply may be directly attached to the measurement cell, thus may be a portion of the measurement cell.

In embodiments of the present invention, the expensive, voluminous and heavy heating block and/or a pre-heating path are avoided and the heating can completely be included in a movable measurement cell. The measurement cell may be movably mounted to support different sample containers. Due to the direct connection of the sample supply at the casing of the measurement cell, an extremely short sample path without the need for moveable connection between the sample supply system and the measurement cell is enabled, avoiding a sealing or a tubing part. Thereby, deterioration of the sample may be reduced or even avoided, in turn enabling an extremely small sample volume, such as between 1 µl and 50 µl, in particular between 5 µl and 30 µl, in particular below 20 µl. Due to the integrated heating, the sample temperature may be brought to the required temperature in a very short time, such as in a time between 1 s and 10 s, in particular below 5 s. The opportunity to move the measurement cell (in particular for feeding a sample into the reception space and/or for measuring) enables to feed all reagents required for the operation into the measurement cell on a short path, thereby reducing the measurement time.

According to an embodiment of the present invention, the measurement cell comprises a combination of features including a polymeric substrate, an integrated heating- and/or temperature detection- and/or temperature regulation system and an attachment of a sample supply system directly at the casing of the measuring cell, while allowing to move the measurement cell.

A measurement apparatus may comprise a temperature regulation system (external to the measurement cell) for controlling the temperature within the measurement cell, in particular the reception space.

In embodiments of the present invention, the sample volume required to perform a measurement of at least one constituent may be minimized and the complexity of the measurement apparatus may be reduced.

It has to be noted that embodiments of the invention have been described with reference to different subject matters. In particular, some embodiments have been described with reference to method type claims whereas other embodiments have been described with reference to apparatus type claims. However, a person skilled in the art will gather from the above and the following description that, unless other notified, in addition to any combination of features belonging to one type of subject matter also any combination between features relating to different subject matters, in particular between features of the method type claims and features of the apparatus type claims is considered as to be disclosed with this document.

The aspects defined above and further aspects of the present invention are apparent from the examples of embodiment to be described hereinafter and are explained with reference to the examples of embodiment. The invention will be described in more detail hereinafter with reference to examples of embodiment but to which the invention is not limited.

BRIEF DESCRIPTION OF THE DRAWINGS

Embodiments of the present invention are now described with reference to the accompanying drawings. The invention is not restricted to the described or illustrated embodiments.

DETAILED DESCRIPTION

Figure 1:
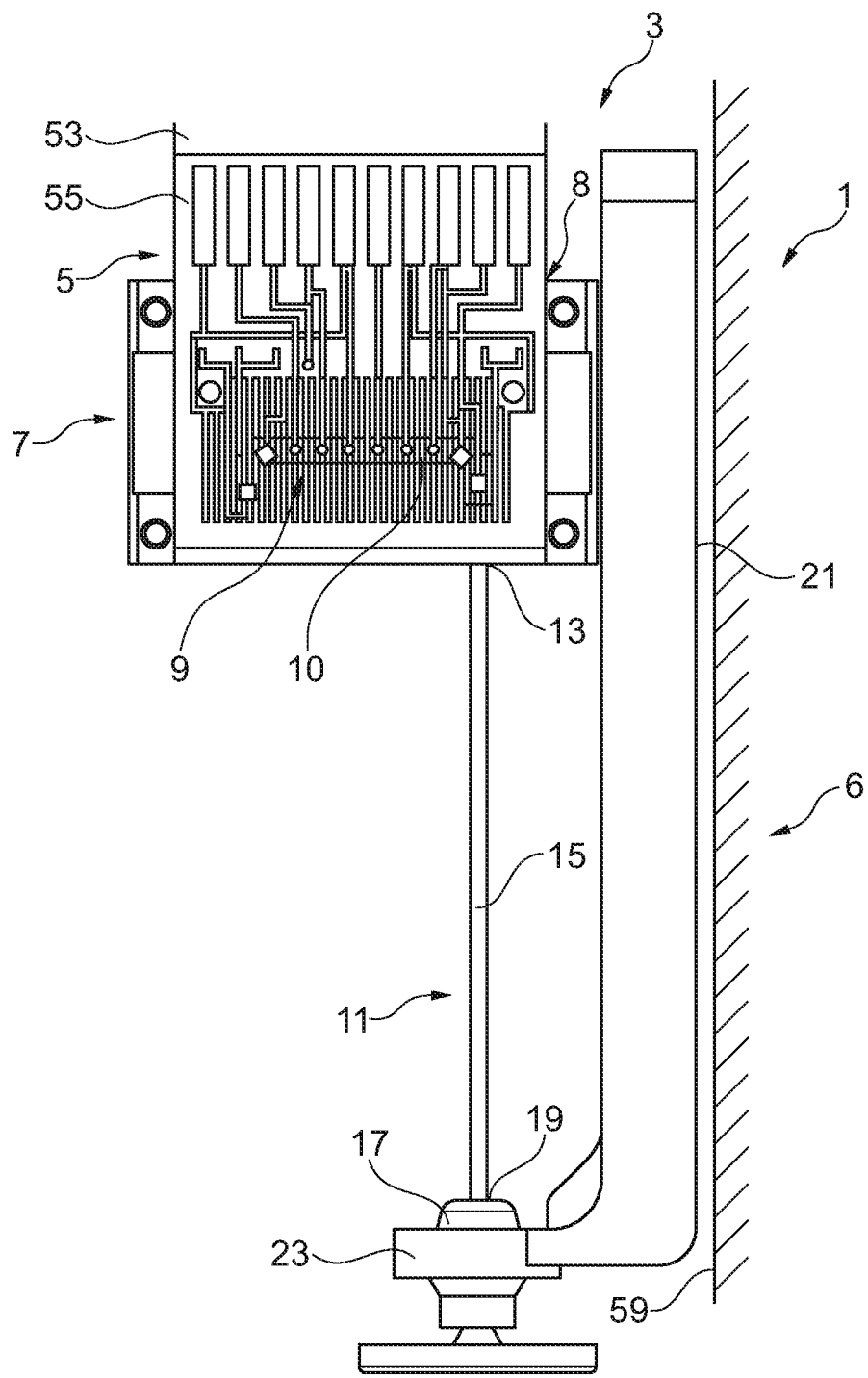
FIG. 1 schematically illustrates (a part of) a measurement apparatus according to an embodiment of the present invention including a movable measurement cell according to an embodiment of the present invention.

FIG. 1 schematically illustrates (a part of) a measurement apparatus 1 according to an embodiment of the present invention including a movable measurement cell 3 according to an embodiment of the present invention and a mounting system 6. The measurement cell 3 includes a first portion 5 comprising a measurement system 8 having at least one sensitive area 10 and the measurement cell 3 further including a (in FIG. 1 only partly visible) second portion 7 which comprises a reception space 9 for the sample.

The first portion 5 and the second portion 7 are connected with each other by gluing such that the sample is in contact with the at least one sensitive area 10 when the sample is located within the reception space 9.

The movable measurement cell 3 further comprises a sample supply system 11 which is (fixedly) attached to an inlet 13 at the second portion 7 of the measurement cell 3 to allow supply of a liquid sample into the reception space 9 without requiring any tubing and/or elastomeric sealing. In other embodiments the inlet 13 is arranged at the first portion 5 and thus also the supply needle is attached to the first portion 5. The sample supply system 11 includes a supply needle 15 connected at one end to the inlet 13 and having a lumen in communication with the reception space 9. The reception space 9 may for example have a volume between 10 µm and 30 µm, in particular substantially or less than 20 µm.

The measurement system 8 includes in the illustrated example five different sensitive areas 10 for measuring the concentration of five different constituents of the sample. The constituents to be measured may for example include ions of K, Ca, Cl, Na and also ions of H. Thus, also the pH may be measured using the measuring system 8.

The measurement apparatus 1 may further comprise (in FIG. 1 not illustrated) a data processing module for processing measurement data obtained from the measurement system 8, an energy supply system for providing electrical energy to components (such as the measurement system, heating/temperature detection system(s)) of the measurement cell, pump(s), valve(s), a user interface, external network capability, access to a database, etc.

Figure 2:
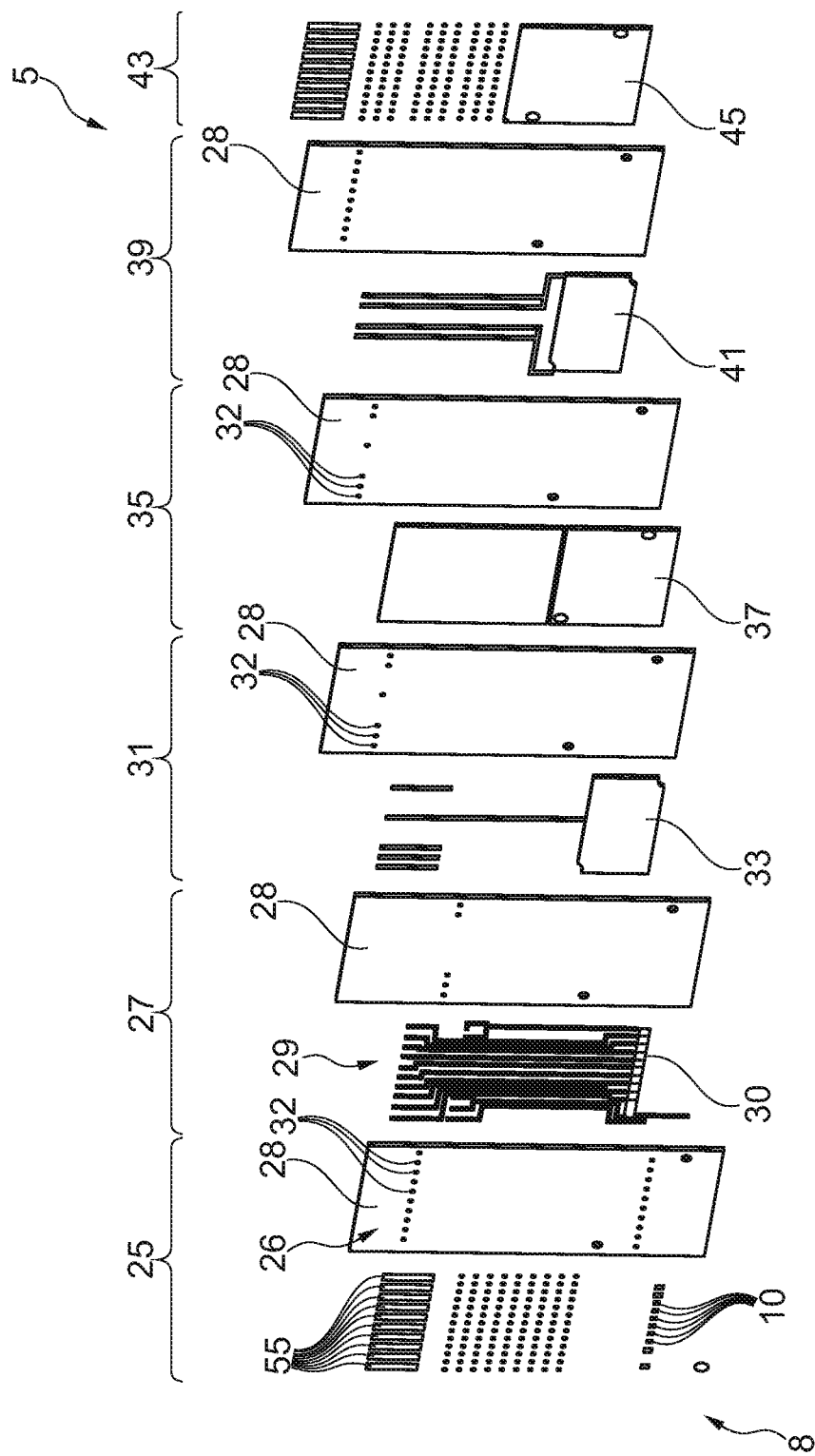
FIG. 2 schematically illustrates a construction of a printed circuit board included in a movable measurement cell according to an embodiment of the present invention.

What is illustrated in FIG. 1 is a projection through the first portion 5 which is formed by a printed circuit board including five layers, as is illustrated in FIG. 2.

The sample supply system 11 further comprises an elastomer element 17 having a through hole 19 through which the supply needle 15 may (partly) be inserted. In the configuration illustrated in FIG. 1, the insertion needle 15 is only partly inserted into the elastomer element 17.

The measurement apparatus 1 illustrated in FIG. 1 further comprises the mounting system 6 that includes a bar 21 having a (in FIG. 1 not illustrated) guiding trail and the mounting system 6 further comprises a supporting portion 23 at one end of the bar for supporting the supply needle 15. In particular, the supporting portion 23 of the mounting system 6 circumferentially engages the elastomer element 17, thereby clamping the elastomer element 17 while the supply needle 15 is partly or at least partly inserted into the through hole 19 of the elastomer element 17. The supporting portion 23 prevents the supply needle 15 from bending during usage of the moveable measurement cell 3.

The mounting system 6 is rotatably fixed at a base 59.

The internal construction of the first portion 5 is schematically illustrated in FIG. 2 in an explosive view. The first portion 5 comprises several layers including a first layer 25 including the measurement system 8 having the sensitive areas 10. The first portion 5 further comprises a second layer 27 which is with an upper layer attached to a lower surface of the first layer 25 and including a heating/temperature detection system 29 which comprises a heating wire 30. An upper surface 26 of a circuit board 28 has the measurement system 8 including the sensitive areas 10 attached to it. With this surface 26 onto which the sensitive areas 10 are attached, the first layer 25 is connected to the second portion 7 of the measurement cell 3, in order to close the reception space 9. Thus, when the sample is filled into the reception space 9, the sample is in direct contact with the sensitive areas 10 of the measurement system 8.

The heating/temperature detection system 29 is attached to a circuit board 28 to form the second layer 27.

The first portion 5 further comprises a third layer 31 comprising a copper plate 33 attached to a circuit board 28, in order to achieve a homogeneous temperature distribution across a region overlapping with a lateral extent of the reception space 9.

The first portion 5 further comprises a fourth layer 35 including a shielding plate 37 and a circuit board 28 onto which the shielding plate 37 is attached. The fourth layer 35 is provided for electrical shielding purposes.

The first portion 5 of the moveable measurement cell 3 further comprises a fifth layer 39 including a further heating/temperature detection system 41 (in particular including a heating wire in a meander configuration). In the embodiment illustrated in FIG. 2 the heating/detection system 29 has the heating wire 30 arranged in a lateral region only slightly larger than (or having substantially a same size as) the lateral extent of the reception space 9. Other dimensions are possible. The further heating/temperature detection system 41 is attached to a circuit board 28 which is thereby also included in the fifth layer of the first portion 5.

The first portion 5 further comprises a sixth layer 43 only including a shielding plate 45 without having an additional circuit board attached.

In other embodiments of the present invention, one or more layers may be omitted and/or the order of the arrangement of the layers may be different from the embodiment illustrated in FIG. 2. For example, the first portion 5 may include only the first layer and the second layer. In other embodiments, the first portion 5 of the moveable measurement cell 3 may include the first layer 25, the second layer 27 and a shielding layer, such as shielding layer 35 or shielding layer 43. Other combinations are possible. Further layers 31 and/or 37 may be omitted.

Figure 3:
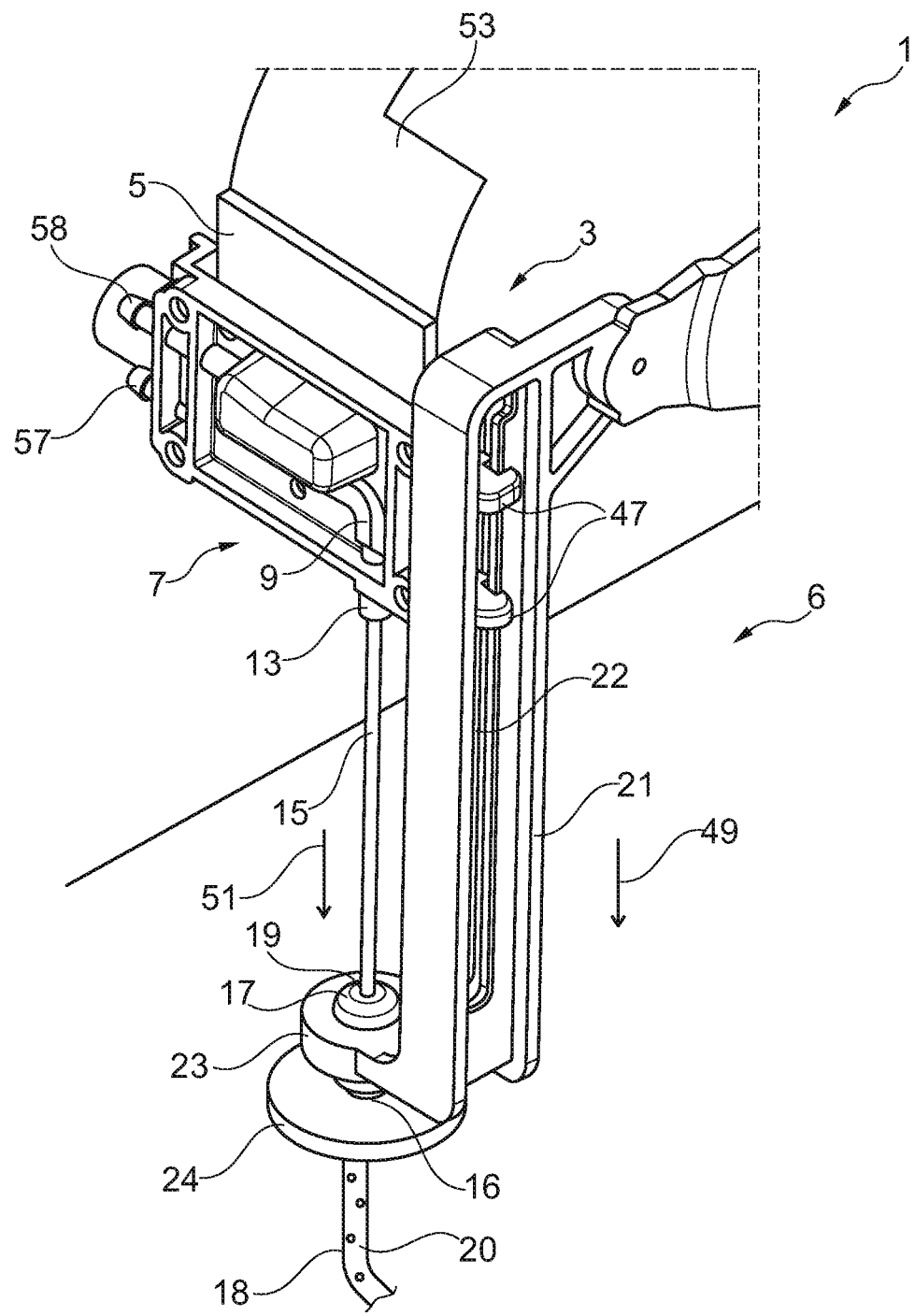
FIG. 3 illustrates a perspective view of (a part of) a measurement apparatus according to an embodiment of the present invention during a purging step.

FIG. 3 schematically illustrates (a part of) a measurement apparatus 1 (illustrated in FIG. 1 in projection) in a perspective view showing the second portion 7 in front of the first portion 5 as it is in particular used during washing/purging and calibrating the moveable measurement cell 3. The mounting system 6 includes a guiding trail 22 on the bar 21. The second portion 7 of the moveable measurement cell 3 has a trail engagement portion 47 here formed as two protrusions protruding through a slot provided by the guiding trail 22. The movable measurement cell 3 may be moved along the guiding trail 22 along the direction 49 which corresponds to the direction 51 of a longitudinal axis of the supply needle 15. During movement of the movable measurement cell 3, the supply needle 15 penetrates through the through hole 19 of the elastomer element 17, allowing to adjust a portion of the supply needle 15 to protrude beyond the supporting portion 23 of the mounting system 6.

For supporting electrical energy to the functional elements and receiving electrical signals from the functional elements comprised in the first portion 5, a cable 53 is connected to respective contact terminals 55 of the first portion 5 of the moveable measurement cell 3. The contact terminals 55 may be contacted from different layers, such as layers 25, 27, 31, 35, 39, 43 by filling through holes 32 within the circuit boards 28 with electrically conducting material.

FIG. 3 also illustrates an outlet 57 and an inlet 58 in communication with the reception space 9. The inlet 58 may serve to supply a solution for a reference electrode.

During supply of a sample via the supply needle 15, a peristaltic pump may be connected (for example using a piping) to the outlet 57 and an end of the supply needle may be immersed in sample to be examined. The sample may then be drawn (by the action of the pump) through the lumen of the supply needle 15 into the reception space 9. Thereupon, the desired temperature (such as 37° C.) may be adjusted by controlling the heating/temperature detection system 29 and/or also operating the further heating/temperature detection system 41. As soon as the temperature has reached the desired temperature and the temperature remains constant within +/−0.2° C., the measurement system 8 may be operated to measure one or more constituents of the sample.

During washing/purging and/or calibration procedure illustrated in FIG. 3 the measurement cell 3 is turned (using e.g. an electric motor in an automatic manner) such that the bar 21 and thus also the supply needle 15 is oriented vertically and such that the elastomer element 17 fits and contacts a washing plate 24, while the supply needle ends within the through hole 19 of the elastomer element 17. The washing plate 24 is fixed at the base 59 by not illustrated mounting elements. The elastomer element 17 presses onto the washing plate 24 and seals a washing and/or calibration solution 20 guided within a piping 18 from leaking out into the environment. Thereby an automatic washing of the supply needle 15 and the entire sample flow path within the measurement cell 3 is enabled and/or a calibration of the measurement system 8 is performed.

Figure 4:
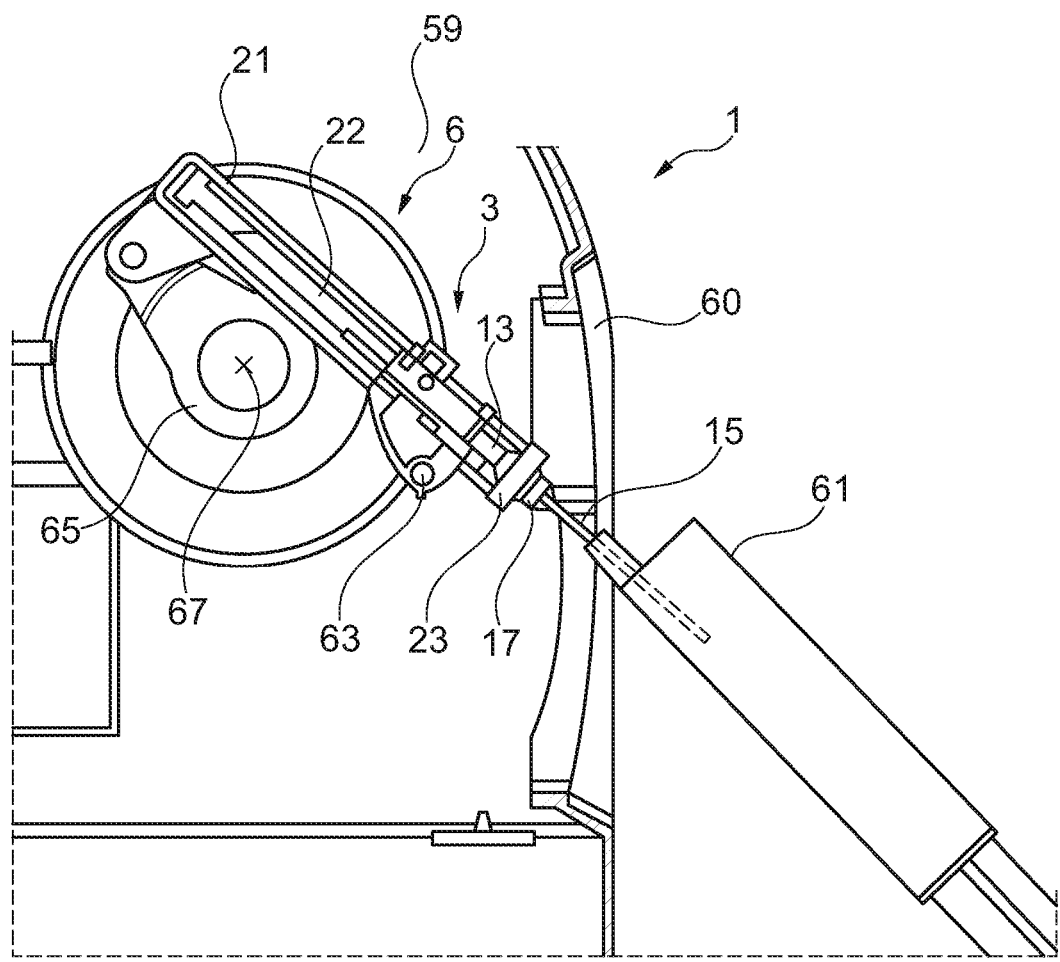
FIGS. 4, 5 and 6 illustrate measurement apparatuses according to embodiments of the present invention during feeding of a sample from different sample sources according to embodiments of the present invention.
Figure 5:
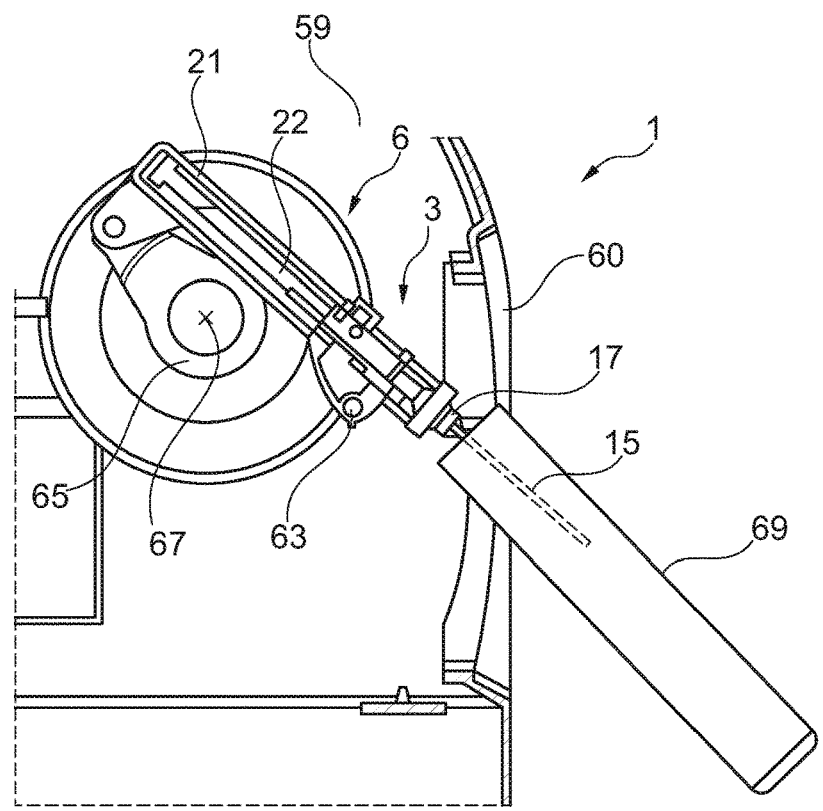
Figure 6:
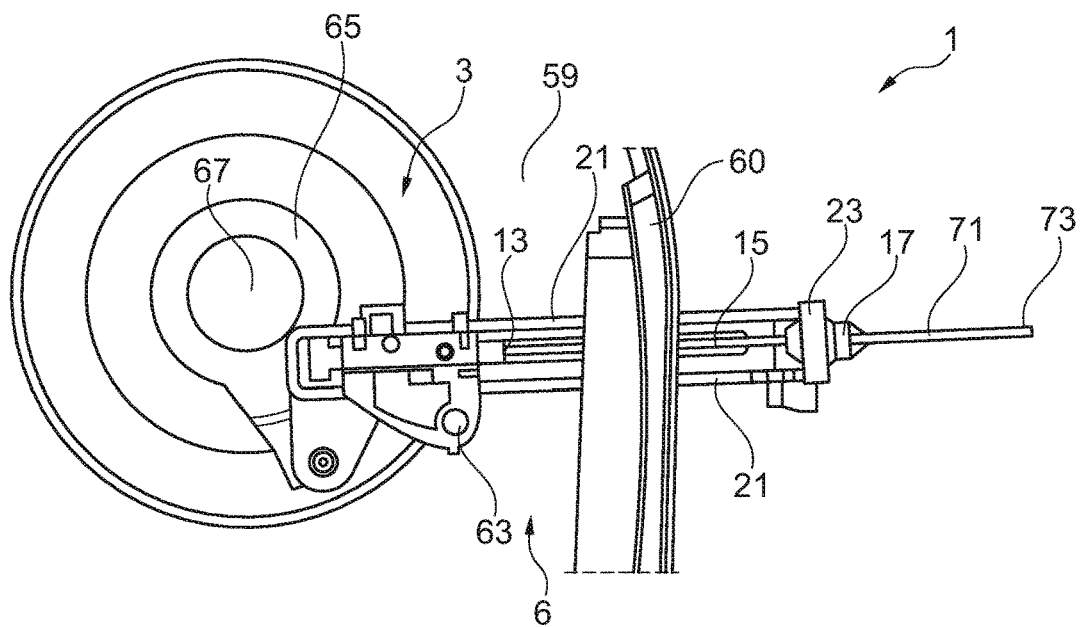

FIGS. 4, 5 and 6 illustrate different configurations of the measurement cell 3 for loading a sample from different sample sources.

FIG. 4 illustrates the case, where a sample is to be loaded into the measurement cell 3 from a syringe 61. The measurement cell 3 is rotatably fixed at the base 59 at one point 63 so that the measurement cell 3 can be swiveled or rotated around the point 63. By rotating the measurement cell 3 around the point 63 it is possible to orient the supply needle 15 such that the end connected to the inlet 13 of the measurement cell 3 is vertically at a higher position, at a same position or at a lower position than another end of the supply needle into which the sample is supplied from an external source, here the syringe 61. In particular, in the situation illustrated in FIG. 4, the end of the supply needle 15 inserted into the syringe 61 is at a vertically lower position than the end of the supply needle 15 connected to the inlet 3 of the measurement cell 3. The bar 21 is at another end apart from the one end where the supporting portion 23 is arranged, rotatably fixed at a portion 65 of the base 59 that can rotate around a rotation center 67. The rotation may be realized using an electric motor that is controlled by (a controller of) the measurement apparatus 1. Rotation around the axis 67 may result in a rotation and/or translation of the measurement cell 3 including the supply needle 15, thereby in particular allowing to adjust different orientations of the supply needle 15.

FIG. 5 illustrates the case, where a sample is to be loaded into the measurement cell 3 from an open container 69, such as an open vacutainer. The orientation of the supply needle 15 and thus the orientation of the measurement cell 3 is similar to the orientation illustrated in FIG. 4.

FIG. 6 illustrates the situation in which a sample is to be loaded into the measurement cell 3 from a capillary 71. In this situation, the orientation of the supply needle 15 is different from the orientation of the supply needle illustrated in FIGS. 4 and 5. In the situation illustrated in FIG. 6, the end of the supply needle 15 into which the sample from the capillary 71 is to be loaded (the side of the supply needle 15 close to the supporting portion 23) is at a vertically higher position than the end of the supply needle close to the inlet 13 of the measurement cell 3. Thereby, it is prohibited that sample runs out of the capillary 71 at an end 73 of the capillary, due to gravity that acts in a vertical downward direction.

The base 59 further comprises an access slit 60 (illustrated in FIGS. 4, 5, 6) through which the bar 21 and/or a part of an external container can slide.

The measurement system 8 may comprise several sensors adapted to measure a concentration of at least one of, in particular ions of, K, Ca, Cl, Na, and/or to measure the pH-value, and/or to measure partial pressure of O2, and/or partial pressure of CO2 And/or to measure the concentrations of Glucose or Lactate.

It should be noted that the term "comprising" does not exclude other elements or steps and "a" or "an" does not exclude a plurality. Also elements described in association with different embodiments may be combined. It should also be noted that reference signs in the claims should not be construed as limiting the scope of the claims.

The invention claimed is:

1. A measurement apparatus for measuring at least one constituent of a liquid sample, the measurement apparatus comprising:
   a movable measurement cell including:
   a first portion comprising a measurement system having at least one sensitive area at a surface of the first portion;
   a second portion comprising at least a part of a reception space for the sample, the second portion being connected to the first portion such that the sample is in contact with the at least one sensitive area when the sample is located within the reception space
   a sample supply system attached to an inlet to allow supply of a liquid sample into the reception space; and
   a trail engagement portion,
   wherein the sample supply system includes a supply needle connected at one end to the inlet, the supply needle having a lumen in communication with the reception space,
   the measurement apparatus further comprising:
   a mounting system configured for movably mounting the movable measurement cell, the mounting system including: a bar having a guiding trail; and a supporting portion at one end of the bar for supporting the supply needle, wherein the trail engagement portion of the measurement cell is configured to engage with the guiding trail for moving the movable measurement cell in a direction of the guiding trail being along a longitudinal direction of the supply needle.

2. The measurement apparatus according to claim 1, the sample supply system further including an elastomer element having a through hole, the supply needle being at least partially inserted into the through hole.

3. The measurement apparatus according to claim 1, wherein the supply needle is adapted to penetrate the through hole of the elastomer element such as to allow supply of a sample into an end of the needle protruding from the elastomer element from a syringe or from a vacutainer and wherein the supply needle when being partially inserted into the through hole of the elastomer element from one side allows supply of a sample from a capillary while the capillary is partially inserted into the through hole of the supply needle from another side.

4. The measurement apparatus according to claim 1, further comprising a heating/temperature detection system integrated into the first portion.

5. The measurement apparatus according to claim 4, wherein the heating/temperature detection system comprising a heating wire temporarily alternatingly used for heating and temperature detection, and wherein the wire is arranged in meandering manner.

6. The measurement apparatus cell according to claim 1, wherein the first portion comprises a polymer formed as a printed circuit board.

7. The measurement apparatus according to claim 6, wherein the printed circuit board comprises several layers including: a first layer including the measurement system; and a second layer having an upper surface attached to a lower surface of the first layer and including the heating/temperature detection system, wherein an upper surface of the first layer is attached to the second portion to partly close the reception space.

8. The measurement apparatus cell according to claim 7, wherein the several layers further including and being attached to each other in that order: a third layer including a heat conducting material for distributing heat generated by the heating/temperature detection system; and/or a fourth layer including an electrically conducting material for electrical shielding; and/or a fifth layer including a further heating/temperature detection system; and/or a sixth layer including an electrically conducting material for electrical shielding.

9. The measurement apparatus according to claim 6, wherein the polymer comprises a fibre-reinforced polymer, wherein fibres of the fibre-reinforced polymer including at least one of glass, carbon, aramid, basalt, paper, wood, asbestos, and wherein the polymer comprises at least one of epoxy, vinylester, polyester thermosetting plastic, phenol formaldehyde.

10. The measurement apparatus according to claim 1, wherein the second portion is integrally formed, manufactured by injection moulding.

11. A measurement apparatus for measuring at least one constituent of a liquid sample, the measurement apparatus comprising:
a movable measurement cell having a trail engagement portion;
a mounting system configured for movably mounting the movable measurement cell, the mounting system including:
a bar having a guiding trail; and
a supporting portion at one end of the bar for supporting the supply needle,
wherein the trail engagement portion of the measurement cell is configured to engage with the guiding trail for moving the movable measurement cell in a direction of the guiding trail being along a longitudinal direction of the supply needle.

12. The measurement apparatus according to claim 11, wherein the supporting portion of the mounting system is adapted to circumferentially engage the elastomer element, thereby clamping the elastomer element while the supply needle is at least partially inserted into the through hole of the elastomer element.

13. The measurement apparatus according to claim 11, the measurement apparatus further comprising a base,
wherein the measurement cell is rotatably fixed at one point to the base, thereby allowing to pivot the measurement cell around the one point to orient the supply needle such that the end connected to the inlet of the measurement cell is selectively vertically at a higher position, at a same position or at a lower position than another end of the supply needle into which the sample is supplied from an external source,
wherein the bar is, at another end apart from the one end where the supporting portion is arranged, rotatably fixed at a portion of the base that can rotate around a rotation center.

14. The measurement apparatus according to claim 13, the measurement apparatus further comprising a washing plate, being fixed at the base and having a through hole,
wherein when the movable measurement cell is appropriately pivoted, the elastomer element contacts the washing plate and seals fluid supplied to the through hole of the washing hole such that the fluid is guided through the through hole of the elastomer element and the lumen of the supply needle to enter the reception space.

15. A method for manufacturing a measurement apparatus for measuring at least one constituent of a liquid sample, the method comprising:
manufacturing a movable measurement cell comprising:
manufacturing a first portion comprising a measurement system having at least one sensitive area at a surface of the first portion;
manufacturing, by injection moulding, a second portion comprising at least a part of a reception space for the sample;
connecting the second portion and the first portion such that the sample is in contact with the at least one sensitive area when the sample is located within the reception space;
providing a trail engagement portion; and
attaching a sample supply system to an inlet to allow supply of a liquid sample into the reception space, wherein the sample supply system includes a supply needle connected at one end to the inlet, the supply needle having a lumen in communication with the reception space,
the method further comprising:
providing a mounting system configured for movable mounting the movable measurement cell, the mounting system including:
a bar having a guiding trail; and
a supporting portion at one end of the bar for supporting the supply needle,
wherein the trail engagement portion of the measurement cell is configured to engage with the guiding trail for moving the movable measurement cell in a direction of the guiding trail being along a longitudinal direction of the supply needle.

16. A method for measuring at least one constituent of a liquid sample, the method comprising:
providing a measurement apparatus according to claim 1;
moving the movable measurement cell such that the sample supply system is in a configuration to allow feeding a liquid sample from an external source into the sample supply system.

17. A method for measuring at least one constituent of a liquid sample, the method comprising:
providing a measurement apparatus according to claim 11; and
moving the movable measurement cell such that the sample supply system is in a configuration to allow feeding a liquid sample from an external source into the sample supply system.

* * * * *